(12) United States Patent
Kopperschmidt (10) Patent No.: US 8,747,663 B2
(45) Date of Patent: Jun. 10, 2014

(54) PROCESS AND DEVICE FOR MONITORING THE SUPPLY OF SUBSTITUTION FLUID DURING AN EXTRACORPOREAL TREATMENT OF BLOOD

(75) Inventor: Pascal Kopperschmidt, Dittelbrunn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 2211 days.

(21) Appl. No.: 11/128,088

(22) Filed: May 11, 2005

(65) Prior Publication Data

US 2006/0254982 A1    Nov. 16, 2006

(30) Foreign Application Priority Data

May 11, 2004  (DE) .......................... 10 2004 023 080

(51) Int. Cl.
*B01D 21/24* (2006.01)
*B01D 24/38* (2006.01)

(52) U.S. Cl.
USPC ............... 210/97; 210/646; 210/741; 210/90; 210/321.6; 604/4.01; 73/592

(58) Field of Classification Search
USPC ........................................... 604/4.01; 73/592
See application file for complete search history.

(56) References Cited

U.S. PATENT DOCUMENTS

| | | | |
|---|---|---|---|
| 6,824,524 B1 | 11/2004 | Favre | |
| 6,827,698 B1 | 12/2004 | Kleinekofort | |
| 2002/0104800 A1* | 8/2002 | Collins et al. | 210/646 |
| 2002/0174721 A1* | 11/2002 | Gross | 73/592 |
| 2007/0108128 A1* | 5/2007 | Kopperschmidt et al. | 210/646 |

FOREIGN PATENT DOCUMENTS

| | | | |
|---|---|---|---|
| DE | 4024434 A1 | 2/1992 | |
| DE | 19917197 C1 | 7/2000 | |
| DE | 101 15 991 | 4/2002 | |
| DE | 10213179 C1 * | 8/2003 | 210/645 |
| EP | 0 189 561 | 8/1986 | |
| EP | 1 348 458 | 10/2003 | |
| WO | WO 00/51664 | 9/2000 | |

OTHER PUBLICATIONS

Translation of DE 10213179, Zhang.*
European Search Report, EP App. No. 10 00 7776, Aug. 19, 2010.

* cited by examiner

*Primary Examiner* — Dirk Bass
(74) *Attorney, Agent, or Firm* — Kenyon and Kenyon LLP (57) ABSTRACT

The invention relates to a process for monitoring the supply of substitution fluid upstream or downstream of a dialyser or filter arranged in an extracorporeal blood stream. One embodiment provides, for the detection of predilution or postdilution, for measuring the pressure in the blood stream downstream of the dialyser or filter, predilution or postdilution being recognized on the basis of the change in pressure following the shutting off and/or starting up of the substituate pump provided for conveying the substitution fluid. Another embodiment provides for recognizing predilution or postdilution on the basis of the comparison of the oscillating pressure signal attributable to the substituate pump to a characteristic reference signal. The characteristic reference signal to which the pressure signal of the substituate pump is compared is preferably the oscillating pressure signal of a blood pump arranged in the blood stream for conveying the blood upstream of the dialyser or filter. In addition, the invention relates to an extracorporeal blood treatment device with a facility for detecting predilution or postdilution, which device operates according to the processes detailed above.

13 Claims, 5 Drawing Sheets

Fourier transformed:

| Standard coefficients of the signals of the arterial blood pump | 0,276 |
|---|---|
| Standard coefficients of the signals of the substituate pump | 0,403 |
| Evaluation | 0,403>>0,276=>post |

Fig. 5A

Fourier transformed:

| Standard coefficients of the signals of the arterial blood pump | 0,265 |
|---|---|
| Standard coefficients of the signals of the substituate pump | 0,177 |
| Evaluation | 0,265≥0,177=>pre |

Fig. 5B

PROCESS AND DEVICE FOR MONITORING THE SUPPLY OF SUBSTITUTION FLUID DURING AN EXTRACORPOREAL TREATMENT OF BLOOD

FIELD OF THE INVENTION

The invention relates to a process for monitoring the supply of substitution fluid for a device for the extracorporeal treatment of blood with an extracorporeal blood stream which includes a first chamber of a dialyser or filter divided by a membrane into the first chamber and a second chamber, and a fluid system which includes the second chamber of the dialyser or filter. In addition, the invention relates to such a device for the extracorporeal treatment of blood using a facility for the detection of the supply of substitution fluid upstream or downstream of the dialyser or filter.

BACKGROUND OF THE INVENTION

For the removal of substances normally contained in the urine and for the withdrawal of fluid, different processes are used in the case of chronic kidney failure for the extracorporeal treatment and/or purification of the blood. In hemodialysis, the blood of the patient is purified outside the body in a dialyser. The dialyser is equipped with a blood chamber and a dialysis fluid chamber which are separated by a semipermeable membrane. During the treatment, the blood of the patient flows through the blood chamber. In order to effectively remove substances normally contained in the urine from the blood, fresh dialysis fluid flows continuously through the dialysis fluid chamber.

While, during hemodialysis (HD), the transportation of the small molecular substances through the membrane is determined mainly by the differences in concentration (diffusion) between the dialysis fluid and the blood, substances dissolved in the plasma water, in particular substances with a higher molecular weight, are effectively removed during hemofiltration (HF) by a high fluid stream (convection) through the membrane of the dialyser. During hemofiltration, the dialyser acts as a filter. Hemodiafiltration (HDF) is a combination of the two methods.

In hemo(dia)filtration part of the serum withdrawn through the membrane is replaced by a sterile substitution fluid which is passed to the extracorporeal blood stream either upstream of the dialyser or downstream of the dialyser. The supply of substitution fluid upstream of the dialyser is also referred to as predilution, and the supply downstream of the dialyser is also referred to as postdilution.

Devices for hemo(dia)filtration are known in the case of which the dialysis fluid is produced online from fresh water and concentrations, and the substitution fluid is produced online from the dialysis fluid.

In the known hemo(dia)filtration devices, the substitution fluid is passed to the extracorporeal blood stream from the fluid system of the machine via a substitution fluid line. In the case of predilution, the substitution fluid line leads to a connecting site on the arterial blood line upstream of the dialyser or filter, whereas during postdilution the substitution fluid line leads to a connecting site on the venous blood line downstream of the dialyser. The substitution fluid line generally exhibits a connector by means of which it can be connected either to the venous or the arterial blood line. To interrupt the fluid supply, a clamp or the like is provided on the substitution fluid line. Such a hemo(dia)filtration device is known, e.g., from EP-A-0 189 561.

Monitoring of the treatment of the blood presupposes the knowledge as to whether the substitution fluid is passed to the extracorporeal blood stream upstream or downstream of the dialyser or filter. Predilution and postdilution, for example, play a part as regards the online clearance measurement (OCM) based on a conductivity measurement since the conductivity of the dialysis fluid downstream of the dialyser depends on whether a predilution or postdilution takes place.

EP-A-1 348 458 A1 describes a process and a device for monitoring the supply of substitution fluid for an extracorporeal blood treatment device. For the detection of the supply of substitution fluid upstream or downstream of the dialyser or filter, the period of operation of the pressure waves of a substituate pump arranged in the substitution fluid line is measured. The supply of substitution fluid upstream or downstream of the dialyser or filter is recognized on the basis of the measurement of the operating time. The known process presupposes the use of a substituate pump producing pressure waves.

DE 101 15 991 C1 describes a device for detecting stenoses in a hose system. The printed document proposes to draw the conclusion of the presence of a stenosis (narrow site) in the hose system in the case of a change in the frequency spectrum of an oscillating pressure signal spreading in the hose system. The operating principle of the known device is based on the fact that the cause of the change in the dynamic behaviour of the hose system is the compliance of the hose system, i.e. the elastic yield under pressure.

SUMMARY OF THE INVENTION

An object of the invention is to indicate a process which allows the recognition of predilution or postdilution with a high level of reliability. In addition, it is an object of the invention to indicate a device for the extracorporeal treatment of blood, wherein the device is equipped with a facility by means of which predilution and postdilution can be reliably recognized.

Different embodiments of the invention are provided; however, the embodiments are based on measuring the pressure in the fluid system downstream of the dialyser or filter.

In one embodiment of the invention, the substituate pump conveying the substitution fluid is shut off and/or started up. The inventor has recognized that the change in the pressure following the shutting off and/or starting up of the substituate pump takes a characteristic course. The supply of substitution fluid upstream or downstream of the dialyser or filter is recognized on the basis of the change in pressure following the shutting off or starting up of the substituate pump. A sudden increase in pressure and/or pressure drop is a parameter characteristic of the change in pressure.

Basically, the recognition can take place only following a change in the pressure after the substituate pump has been shut off or started up. A greater reliability, however, can be achieved if the recognition of the predilution or postdilution takes place on the basis of the change in pressure both during the shutting down and the starting up of the substituate pump or vice versa.

In a preferred embodiment of the invention which allows the recognition of predilution and postdilution with a particularly high reliability level, the substituate pump which has been started up is shut off and after a predetermined time interval started up again, the pressure being measured downstream of the dialyser or filter. A supply of substitution fluid upstream or downstream of the dialyser or filter is recognized on the basis of the change between a previous increase in pressure and a subsequent pressure drop or between a previous pressure drop and a subsequent increase in pressure.

If a sequence of pressure increase and pressure decrease is detected, the conclusion is drawn that the supply of substitution fluid takes place downstream of the dialyser or filter, whereas the conclusion is drawn that the supply of substitution fluid takes place upstream of the dialyser or filter if a sequence of a pressure decrease and an increase in pressure is detected.

One advantage in this embodiment of the invention consists of no pressure pulses being evaluated which propagate themselves in the blood stream. Consequently, it is not necessary to provide a substitute pump producing an oscillating pressure pulse in order to be able to differentiate between post-dilutive and pre-dilutive substitution.

To suppress interference signals, the pressure signal is preferably filtered with a low-pass filter.

The characteristic pulse sequence following the stop and start of the substitute pump can take place on the basis of a comparison of the pressure signal in the blood stream downstream of the dialyser or filter with an upper and lower limit value which is characteristic of an increase in pressure or pressure drop attributable to predilution or postdilution.

The facility for the detection of the supply of substitution fluid upstream or downstream of the dialyser or filter of the extracorporeal blood treatment device according to an embodiment of the invention is equipped with a control unit for shutting off and/or starting up the substitute pump, a measuring unit for measuring the pressure in the blood stream downstream of the dialyser or filter and an evaluation unit. The evaluation unit is designed such that a supply of substitution fluid upstream or downstream of the dialyser or filter is recognized on the basis of the change in the venous pressure after shutting down and/or starting up the substitute pump.

The measuring unit for measuring the venous pressure is preferably equipped with a venous pressure sensor and a low-pass filter connected to the signal output end of the pressure sensor.

The evaluation unit is preferably equipped with a comparator which compares the output signal of the pressure sensor for the detection of an increase in pressure and/or pressure drop with a predetermined upper and/or lower limit value.

The process according to an embodiment of the invention and the device according to an embodiment of the invention are advantageously used for determining the dialysis dosage using the so-called online clearance monitoring (OCM), and in the case of a substitute supply as a function of the blood flow. In addition, the process and the device provide for decision-making assistance regarding all relevant parameters relating to dialysis if a distinction is necessary between the post-dilutive and the pre-dilutive substitute administration. The process and the device may also be used for the determination of the blood flow, the determination of the shunt or fistula recirculation, the monitoring of the relative blood volume and/or hematocrit, the determination of the filling volumes of the dialyser or filter and the recognition of the venous needle type.

Most of the components necessary for the detection facility are generally already present in the known blood treatment devices. For example, it is possible to make use of the venous pressure sensor for measuring the pressure in the blood stream downstream of the dialyser or filter. A microprocessor control is also available. Consequently, the expenditure for the present invention in terms of equipment is relatively low.

Another embodiment of the invention presupposes the use of a substitute pump producing pressure waves. The supply of substitution fluid upstream or downstream of the dialyser or filter is recognized by means of a characteristic reference signal on the basis of the comparison of the oscillating pressure signal which propagates itself within the blood stream and is attributable to the substitute pump. The process and the device according to this embodiment of the invention are based on the fact that the frequency spectrum of the oscillating pressure signal depends on whether the pressure signal propagates itself via the dialyser in the case of predilution or not via the dialyser in the case of postdilution. Also, the amplitude of the pressure pulse changes as a function of predilution or postdilution.

In the case of the known blood treatment devices, the oscillating pressure signal of the substitute pump which propagates itself within the extracorporeal blood stream is superimposed by further pressure signals which are attributable, for example, to the blood pump arranged within the blood stream upstream of the dialyser or filter or to facilities arranged within the fluid system which include, for example, the concentrate pump, the ultrafiltration pump or the balance chamber. For this reason, the pressure signal attributable to the substitute pump is obtained from the pressure signal measured in the blood stream. To avoid errors of measurement, the dialyser or filter can also be separated from the fluid system.

A preferred embodiment of the invention which allows detection of the supply of substitution fluid with a particularly high reliability level provides, as characteristic reference signal, the signal of the blood pump arranged in the extracorporeal blood stream upstream of the dialyser or filter, which pump also produces oscillating pressure signals. This embodiment is based on the assumption that, during predilution, the oscillation of the pressure signals of the blood pump and the substitute pump which propagate themselves through the dialyser and the hose system, differs only insignificantly. In the case of postdilution, on the other hand, the oscillation of the pressure signals of the substitute pump and the blood pump differs substantially since the pressure signals of the substitute pump do not propagate themselves via the dialyser. In this way, not only a relative but also an absolute distinction characteristic is obtained between predilution and postdilution.

To obtain the pressure signals of the blood pump and the substitute pump, a Fourier analysis of the pressure signal measured downstream of the dialyser or filter is preferably carried out. From the pressure signals of the substitute pump and the blood pump, the amplitudes of at least two harmonic components are preferably determined. At least one first evaluation factor is determined from at least one quotient of at least one harmonic component of higher order and at least one harmonic component of lower order of the substitute pump, and at least a second evaluation factor is determined from at least one quotient of at least one harmonic component of higher order and at least one harmonic component of lower order of the blood pump.

In practice, it has proved to be sufficient if, by way of the Fourier transformation, the coefficients of the second or higher harmonic of the pressure signal of the blood pump and/or substitute pump are standardized with respect to the coefficient of the first harmonic of the pressure signal of the blood pump and/or substitute pump in order to form the two evaluation factors.

The conclusion that a postdilution takes place is drawn if the difference between the first evaluation factor and the second evaluation factor is greater than a predetermined limit value whereas the conclusion that predilution takes place is drawn if the difference between the first evaluation factor and the second evaluation factor is smaller than the predetermined limit value.

The facility for the detection of the supply of substitution fluid to the extracorporeal blood treatment device according to an embodiment of the invention is equipped with a measuring device for measuring the pressure in the blood stream downstream of the dialyser or filter and an evaluation unit which in turn is equipped with means for obtaining the oscillating pressure signal attributable to the substituate pump, means for comparing the oscillating pressure signal with a characteristic reference signal and means for detecting predilution or postdilution on the basis of a comparison of the oscillating pressure signal of the substituate pump with the characteristic reference signal.

A distinction between predilution and postdilution can be made at the beginning of the dialysis treatment alone by evaluating the pressure signal of the substituate pump, but preferably in conjunction with the pressure signal of the blood pump.

Apart from the measuring unit for measuring the pressure in the extracorporeal blood stream downstream of the dialyser or filter which is, in general, part of the known blood treatment devices, no further hardware components are required.

DETAILED DESCRIPTION

In the following, embodiments of the process according to the invention and embodiments of the blood treatment device according to the invention are explained in further detail with reference to the figures.

Figure 1:
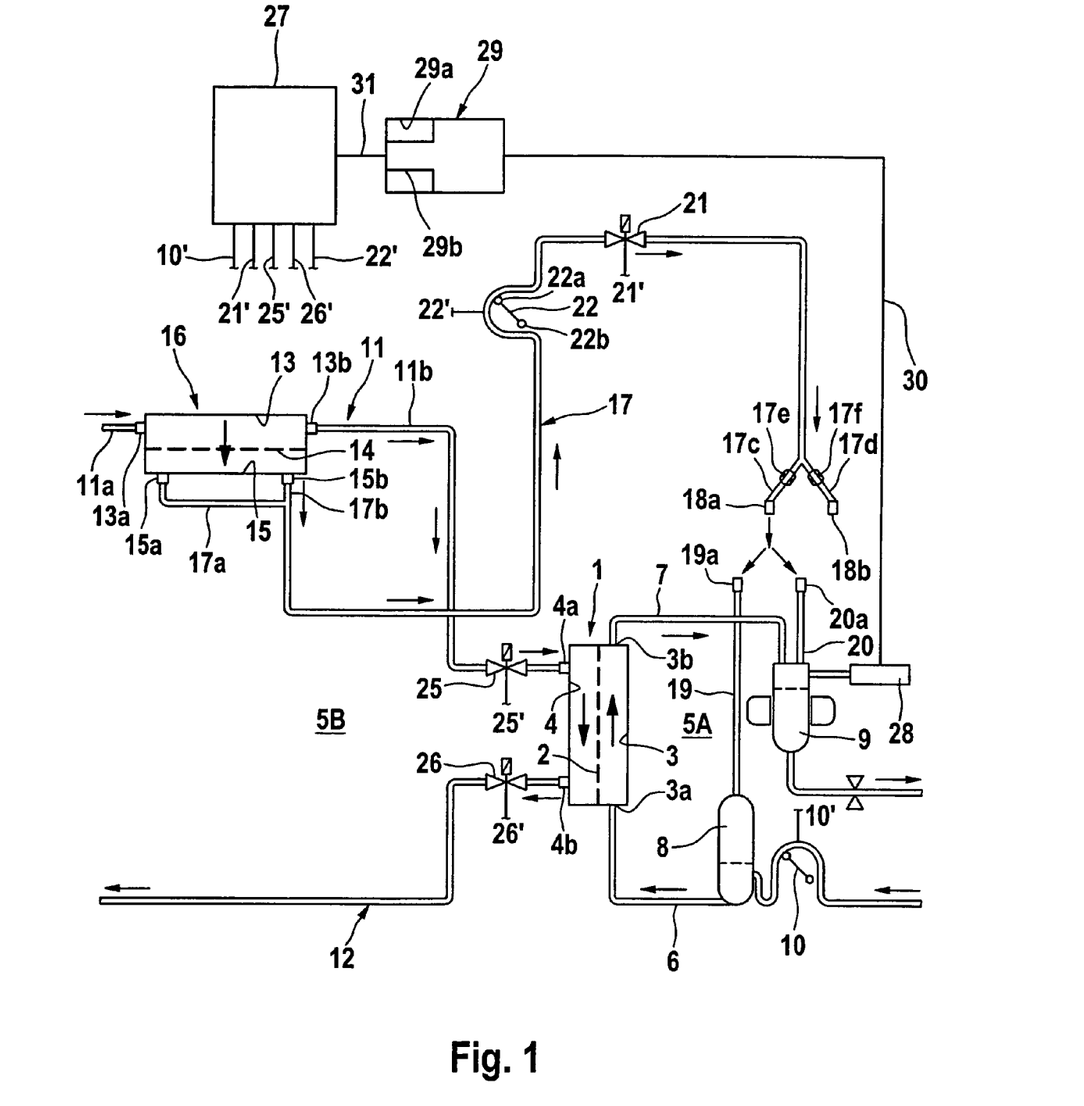
FIG. 1 is a greatly simplified diagrammatic representation of an embodiment of a device according to the invention for the extracorporeal treatment of blood with a facility for detecting predilution and postdilution.

FIG. 1 shows a simplified diagrammatic representation of the essential components of a hemo(dia)filtration device together with a facility for the detection of the supply of substitution fluid in the extracorporeal blood stream upstream or downstream of the dialyser or filter. When we speak of a dialyser in the following, this should be understood to include a filter.

The hemo(dia)filtration device is equipped with a dialyser 1 which is separated by a semipermeable membrane 2 into a first chamber 3 through which blood flows and a second chamber 4 through which a dialysis fluid flows. The first chamber 3 is operated in an extracorporeal blood stream 5A whereas the second chamber 4 is operated in the fluid system 5B of the hemo(dia)filtration device.

The extracorporeal blood stream 5A comprises an arterial blood line 6 which leads to the inlet 3a of the blood chamber 3 and a venous blood line 7 which leads from the outlet 3b of the blood chamber 3 of the dialyser 1. To eliminate air bubbles, an arterial drip chamber 8 is inserted into the arterial blood line 6 and venous drip chamber 9 into the venous blood line 7. The patient's blood is conveyed through the blood chamber of the dialyser by means of an arterial blood pump 10, in particular a roller pump, which is arranged on the arterial blood line 6.

The fluid system 5B comprises a dialysis fluid feed line 11 which leads to the inlet 4a of the dialysis fluid chamber 4 and a dialysis fluid discharge line 12 which leads from the outlet 4b of the dialysis fluid chamber 4 of the dialyser 1. Fresh dialysis fluid flows via the dialysis fluid feed line 11 from a dialysis fluid source, which is not illustrated, into the dialysis fluid chamber whilst the spent dialysis fluid is discharged from the dialysis fluid chamber via the dialysis fluid discharge line 12 to a drain line which is not illustrated. The balancing device which is generally provided in the hemo(dia)filtration devices for balancing fresh with spent dialysis fluid is not illustrated for the sake of clarity. Also, additional facilities for purifying and rinsing the system are not illustrated.

The dialysis fluid supply line 11 comprises a first section 11a which leads to the inlet 13a of a first chamber 13 of a sterile filter 16 subdivided by a membrane 14 into the first chamber and a second chamber 15, and a second section 11b which leads from the outlet 13b of the first chamber 13 of the filter 16 to the inlet 4a of the dialysis fluid chamber 4.

During dialysis treatment, the dialysis fluid, for example, can be supplied from the fluid system 5B as substitution fluid via a substitution fluid line 17 to the extracorporeal blood stream 5A. The fluid line 17 is equipped at both ends with two line sections 17a, 17b, 17c, 17d respectively. Line section 17a is connected with the first outlet 15a of the sterile filter 16 and line section 17b is connected with second outlet 15b, whereas a connector 18a, 18b is connected to line sections 17c and 17d. By means of the two connectors 18a, 18b, the substitution fluid line 17 can be connected to a connecting line 19 leading to the arterial drip chamber 8 and/or to a connecting line 20 leading to the venous drip chamber 9. The connecting lines 19, 20 are equipped for this purpose with corresponding connections 19a, 20a. Hose clamps 17e, 17f are fitted to the hose line sections 17c, 17d, by means of which clamps a fluid connection can optionally be established to the arterial or venous drip chamber 8, 9. It is also possible for the substitution fluid line 17 to be connected with both connecting lines 19, 20 and both hose clamps 17e, 17f to be open.

To clamp the substitution fluid line 17 shut, a shut-off device 21, e.g. a hose clamp, is provided downstream of the sterile filter 16, which clamp is preferably operated electromagnetically. The substitution fluid is conveyed by means of an occlusion pump, in particular a roller pump 22, into which the substitution fluid line 17 is inserted. Such roller pumps are part of the state of the art. They are equipped with several rolls 22a, 22b by means of which the cross-section of the hose line for conveying the fluid can be reduced. In this way, pressure waves are formed which are capable of propagating themselves in both directions through the substitution fluid line. In should be noted that an occlusion pump producing pressure waves is not required as substitute pump in the case of this embodiment of the blood treatment device according to the invention. Instead, a substitute pump which does not produce pressure waves can be used to convey the substitution fluid. This is one advantage of this embodiment.

To uncouple the dialyser 1 from the fluid system 5B, an electromagnetically operable shut-off device 25, 26 is provided respectively in the dialysis fluid feed line 11 upstream of the dialyser 1 and in the dialyser fluid discharge line 12 downstream of the dialyser 1.

The blood pump 10, the substitute pump 22 and the shut-off devices 21, 25 and 26 are connected via control lines 10', 22', 21', 25' and 26' with a central control unit 27 by means of which the individual components are controlled taking the predetermined treatment parameters into consideration.

To operate the hemo(dia)filtration device as a hemodialysis device, the shut-off device 21 is closed causing the dialysis fluid to flow through the dialysis fluid chamber 4 of the dialyser. To operate the hemo(dia)filtration device as a hemo(dia)filtration device, the shut-off device 21 is opened such that sterile dialysis fluid flows from the sterile filter 16 as substitution fluid optionally into the arterial drip chamber 8 (predilution) or the venous drip chamber 9 (postdilution). However, it is also possible to operate the hemo(dia)filtration device merely as a hemofiltration device if the supply of dialysis fluid to the dialysis fluid chamber 4 of the dialyser is interrupted. To interrupt the fluid supply, the shut-off device 25 is closed upstream of the dialyser.

The facility for the detection of predilution and postdilution is equipped with a control unit which forms part of the central control unit 27 of the blood treatment device. In addition, the detection facility is equipped with a measuring unit 28 for measuring the pressure in the extracorporeal blood stream downstream of the dialyser 1 and with an evaluation unit 29. A pressure sensor 28 fitted to the drip chamber 9 is provided as measuring unit, which sensor produces an electrical pressure signal as a function of the venous pressure. The pressure signal of the pressure sensor 28 is passed via a data transmission line 30 to the evaluation unit 29 which in turn is connected via a data transmission line 31 with the control unit 27. The evaluation unit 29 is equipped with a low-pass filter 29a for filtering the pressure signal of the pressure sensor 28 and with a comparator 29b by means of which the pressure signal is compared with a predetermined upper and lower limit value.

In the following, the detection of the supply of substitution fluid upstream or downstream of the dialyser is described in detail. The control unit 27 of the detection facility shuts off the substitute pump 22 which is already running, preferably at the beginning of the blood treatment, in order to initiate the measurement. On completion of a predetermined time interval, the control unit 27 starts up the substitute pump 22 again. While the substitute pump is shut off, the pressure sensor 28 measures the venous pressure. The venous pressure signal of the sensor 28 filtered by means of the low-pass filter 29a is compared in the comparator 29b of the evaluation unit 29 with an upper and lower limit value in order to detect either an increase in pressure after the shutting off of the substitute pump and a pressure drop after the start up of the substitute pump, or a decreases in pressure after the shutting off of the substitute pump and an increase in pressure after the start up of the substitute pump.

Figure 2A:
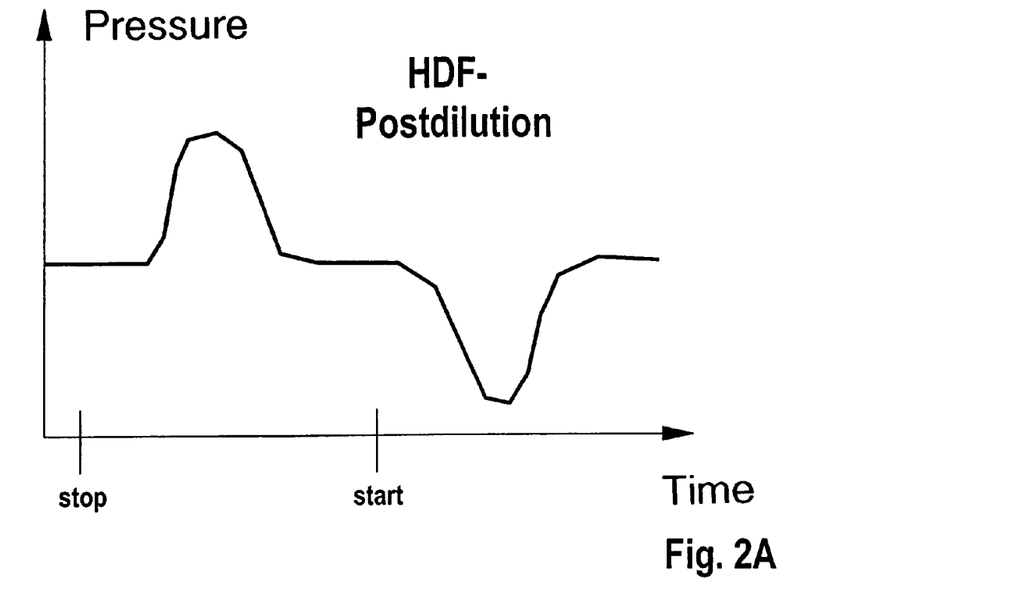
FIG. 2A shows a basic illustration of an example of the change of the pressure, over time, in the extracorporeal blood stream downstream of the dialyser or filter in the case of postdilution.
Figure 2B:
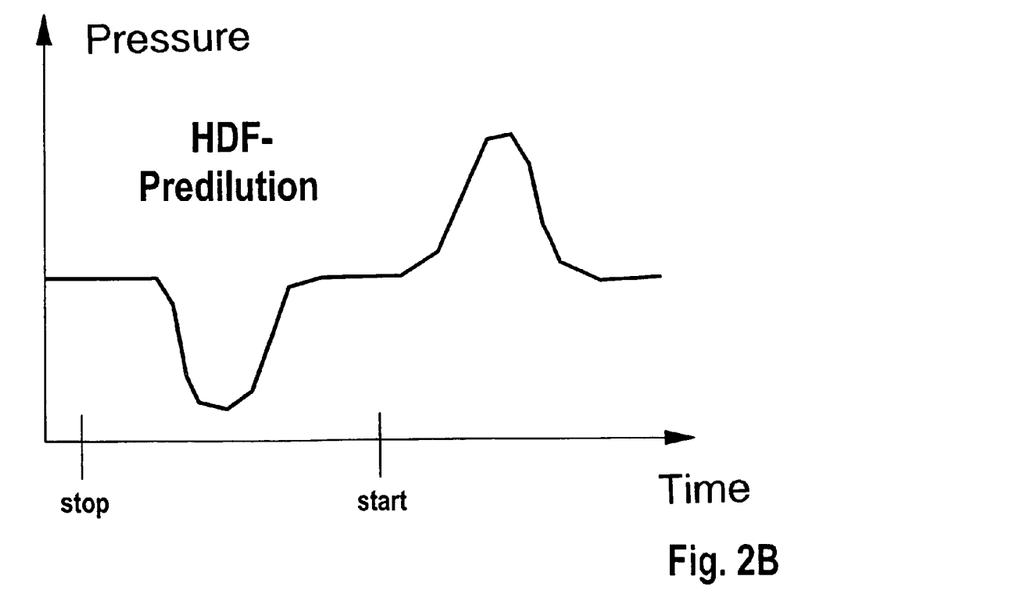
FIG. 2B shows a basic illustration of an example of the change, over time, of the venous pressure in the case of predilution.

FIG. 2A shows the basic change in the venous pressure over time in the case of postdilution, and FIG. 2B shows the change in pressure over time in the case of predilution. It can be clearly seen that the pressure initially increases in the case of post-dilution in order to decrease subsequently. In the case of predilution, the pressure decreases at first in order to increase subsequently. On the basis of these two characteristic changes, the evaluation unit recognizes whether postdilution or predilution is present. The result can be indicated optically and/or acoustically on a display unit which is not illustrated.

Figure 3A:
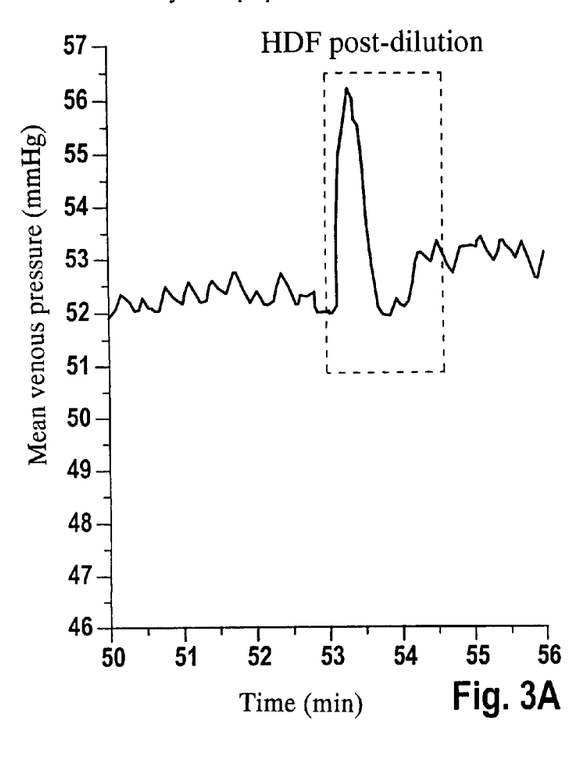
FIG. 3A shows the average venous pressure measured during an in vitro HDF dialysis treatment as a function of the time in the case of postdilution
Figure 3B:
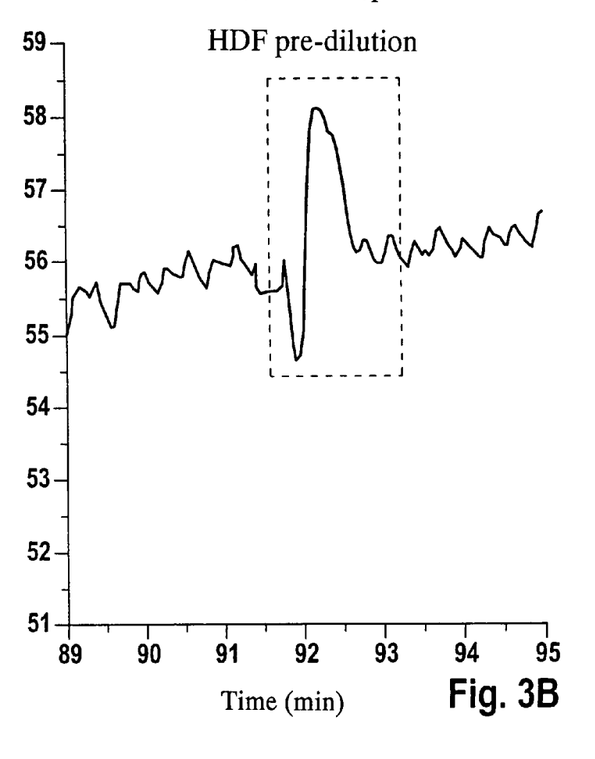
FIG. 3B shows the average venous pressure in the case of predilution.

FIGS. 3A and 3B show the venous pressure as a function of time in the case that the predetermined time interval during which the substitute pump is shut off is relatively long. If a shorter time interval is provided, the maximums and/or minimums lie closer together. To initiate the measurement, the substitute pump which has already been started up is shut-off for a predetermined time interval. In principle, however, it is also possible to start up the substitute pump which had initially been shut-off, for a predetermined time interval.

The characteristic change in the pressure signal shown in FIGS. 2A and 2B is attributable to the changed viscosity of the blood during predilution or postdilution. In the case of postdilution, the viscosity of the blood is reduced as a result of the supply of substitution fluid in the venous blood line 7 downstream of the drip chamber 9. When the substitute pump 22 is shut-off, the viscosity of the blood increases in this section of the venous blood line. Consequently, an increased pressure drop occurs on the venous needle. As a result, the venous pressure increases. If the substitute pump is restarted, the viscosity of the blood in the venous blood line 7 downstream of the drip chamber 9 decreases such that the venous pressure drops. As a result, a pressure pulse with a positive sign occurs following the stopping of the substitute pump and a pressure pulse with a negative sign occurs after the start up of the pump (FIG. 2A). The pulse width depends on the ratio of the blood volume between the dialysis fluid chamber 4 of the dialyser 1 and the drip chamber 9 as well as the blood flow. In the case of predilution, on the other hand, the sequence of the signs of the pressure pulse is reversed following the shutting off and the starting up of the substitute pump. In the case of the stopping of the pump, a pressure drop occurs and a pressure increase following the start up of the pump (FIG. 2B).

FIGS. 3A and 3B show the average venous pressure (mmHg) as a function of the time during an in vitro HDF dialysis treatment, the blood flow being adjusted to 250 ml/min, the substitution rate for predilution and postdilution to 70 ml/min and the rate of ultrafiltration to 0 ml/h. In practice, it has been found that the amplitudes of the pressure increase or pressure drop differ from each other. However, the pressure increase or pressure decrease is clearly recognizable both in the case of predilution and postdilution. The predetermined upper and lower limit values must be set such that they are below or above the maximums or minimums. On the other hand, however, the upper and lower limit values should be above or below the pressure variations which are superimposed over the pressure signal.

On the basis of the positive and/or negative pressure pulses a conclusion can also be drawn regarding the fistula circulation. A repetition of the pressure pulse sequence which can be detected in the venous blood line 7 with the venous pressure sensor 28, and in the arterial blood line 6 which can be detected with the arterial pressure sensor, points towards a recirculation. The ratio between the integral of the pressure signal of the arterial pressure sensor in a predetermined time interval in which the repeating negative and/or positive pressure pulse occurs and the integral of the pressure signal of the venous pressure sensor 28 in a predetermined time interval in which the negative and/or positive pressure pulse occurs is used as a measure of the recirculation. The recirculation Rec [%] is calculated according to the following equation:

$$Rec[\%] = 100 \cdot \left( \frac{\int P_{art} dt}{\int P_{ven} dt} \right)$$

It is possible to draw a conclusion from the time difference (Δt) between the beginning and the end of the pressure pulse increase or the pressure pulse decrease, if the blood feed rate ($Q_b$) is known, regarding the volume of fill ($V_{PD}$) of the hose segment between the inlet 4a of the dialysis fluid chamber 4 of the dialyser 1 and the connecting site of the substitution fluid line 17, 20 to the drip chamber 9. The volume can be calculated according to the following equation:

$$V_{PD} = Q_b \Delta t = Q_b (t_{End} - t_{Beginning})$$

In addition, it is possible to draw a conclusion regarding the volume of fill ($V_{PD}$) of the hose segment between the inlet 4a of the dialysis fluid chamber 4 and the venous needle if, in the case of HDF predilution, the predetermined time interval between the shut-off of the substituate pump 22 and the beginning of the pressure drop and/or the time interval between the start up of the substituate pump and the beginning of the pressure increase is multiplied by the blood feed rate ($Q_b$). In the case of HDF postdilution, an analogous connection exists, the pressure difference between the stoppage of the substituate pump and the beginning of the pressure pulse increase and/or the time difference between the start of the substituate pump and the beginning of the pressure pulse drop being monitored.

In a converse manner, the true blood flow can be determined if the volume of fill of the hose segments mentioned above and the time differences are known respectively.

If the connection between the hematocrit, the blood pressure drop and/or the blood pressure increase, the blood feed rate and needle geometry are known, the amplitude of the pressure increase and/or decrease provides information on the type of needle. If the type of needle is known, the corresponding conclusion can be drawn regarding the hematocrit.

In this way, the change in the hematocrit can be monitored during the dialysis treatment by way of the change in the amplitude of the pressure pulses.

Figure 4:
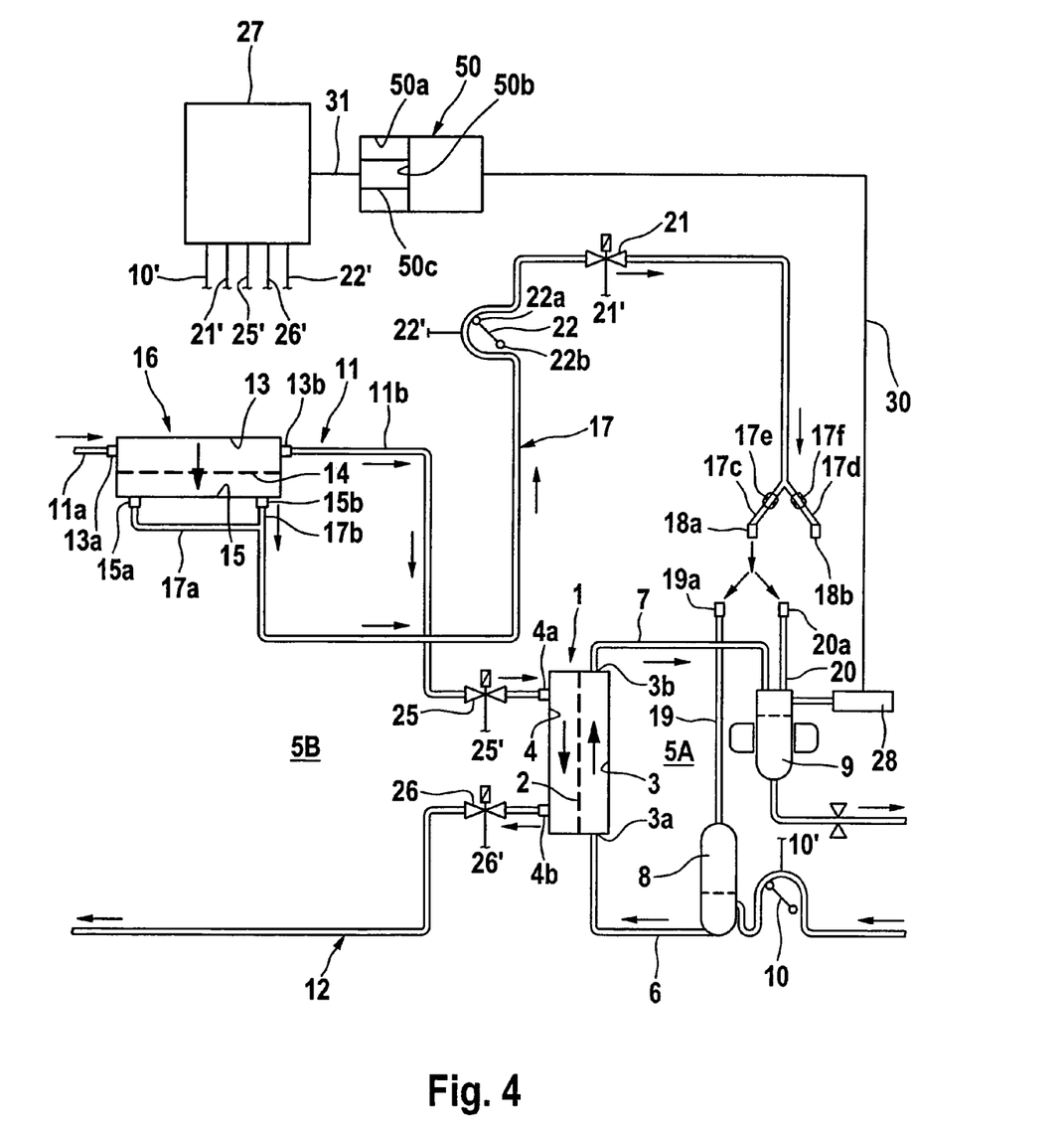
FIG. 4 is a greatly simplified diagrammatic representation of another embodiment of the extracorporeal blood treatment device according to the invention.

FIG. 4 shows an alternative embodiment of the blood treatment device according to the invention in a simplified diagrammatic representation. With the exception of the facility for the detection of predilution or postdilution, the blood treatment device of FIG. 4 does not differ from the blood treatment device of FIG. 1. For this reason, the components corresponding to each other are indicated by the same reference signs.

The detection facility is also equipped with a venous pressure sensor 28 for measuring the pressure in the venous blood line 7. The evaluation unit 50 receives the venous pressure signal of the pressure sensor 28 via the data transmission line 30. The evaluation unit 50 is equipped with a facility for the Fourier analysis 50a which carries out a Fourier analysis of the venous pressure signal.

The process for the detection of predilution or postdilution presupposes that the substituate pump 22 and the pressure pump 10 are pumps producing pressure waves such as occlusion pumps, in particular roller pumps. Since the frequency of the pressure waves produced by the blood pump 10 is very much higher, as a result of the very much higher speed of the blood pump in comparison with the substituate pump, than the frequency of the pressure waves of the substituate pump, the pressure waves of the blood pump can be distinguished from those of the substituate pump. In the case of predilution, the pressure waves of the substituate pump 22 pass through not only the hose section of the substitution fluid line 17, 19, but also the hose section of the arterial blood line 6 between the drip chamber 8 and the inlet 3a of the blood fluid chamber 3, the blood fluid chamber and the venous blood line 7 before reaching the pressure sensor 28. In the case of postdilution, the pressure waves, on the other hand, do not pass through the blood fluid chamber and the corresponding blood line sections. The effect of the blood fluid chamber 3 and the associated blood line sections can be described as being a transmission function. When the dialyser and the associated line sections are situated in the transmission path of the pressure waves, the dynamics of the pressure pulses and their frequency spectrum change, higher frequencies, in particular, being more strongly attenuated.

An accurate knowledge of the transmission function is not necessary for the detection of predilution or postdilution. It is sufficient if a relationship is established between the pressure signal of the substituate pump and the pressure signal of the blood pump.

The pressure signal measured with the pressure sensor 28 contains both the pressure signal of the blood pump 10 and that of the substituate pump 22. The facility for the Fourier transformation 50a of the evaluation unit 50 breaks down the pressure signal of the blood pump 10 and the substituate pump 22 measured with the pressure sensor 28 into the signal components attributable to the blood pump and/or the substituate pump.

Figure 5A:
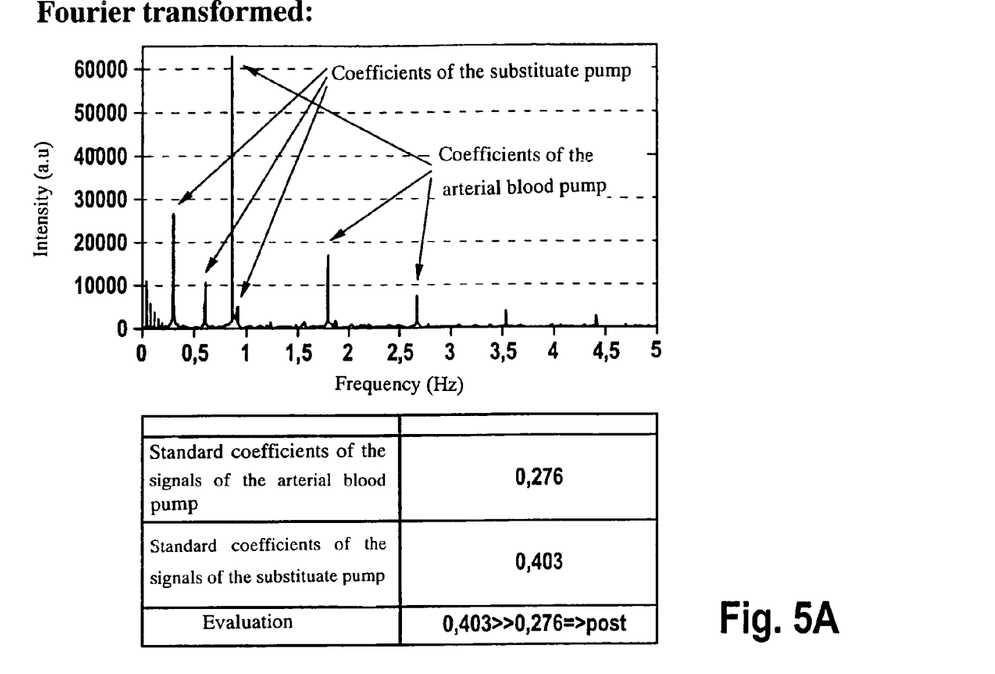
FIG. 5A shows an example of the frequency spectrum of the pressure waves in the extracorporeal blood stream which are attributable to the substituate pump and the blood pump and a table with standardized coefficients of the pressure signals of the blood pump and the substituate pump in the case of postdilution.
Figure 5B:
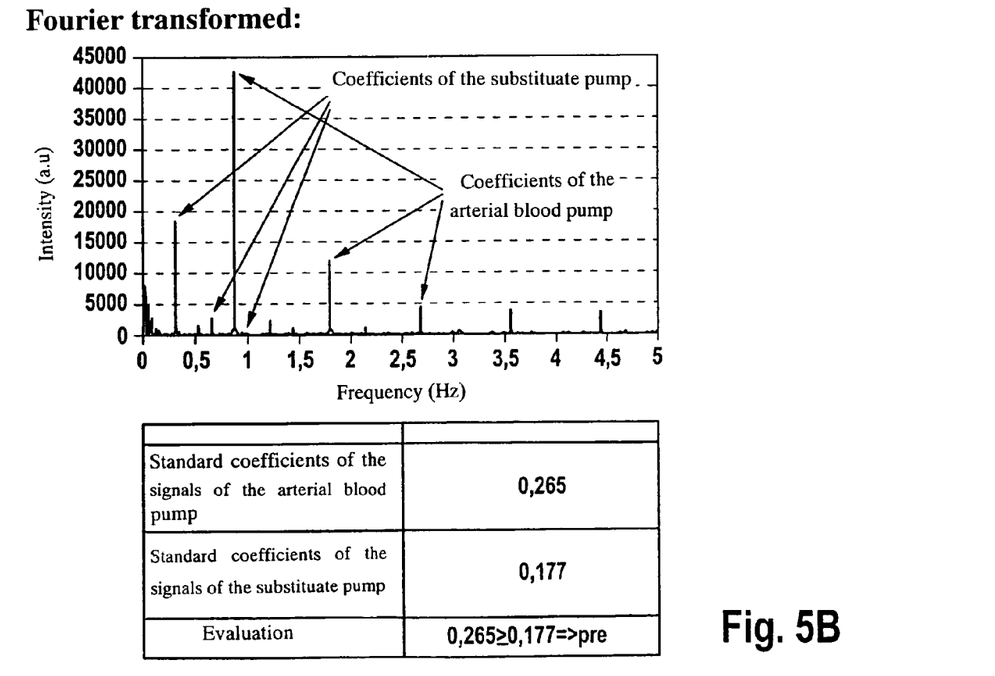
FIG. 5B shows an example of the frequency spectrum of the pressure waves in the extracorporeal blood stream which are attributable to the substituate pump and the blood pump and a table with standardized coefficients of the pressure signals of the blood pump and the substituate pump in the case of predilution.

FIGS. 5A and 5B show the frequency spectrum of the venous pressure signal determined by the Fourier transformation in the case of postdilution or predilution. The measured values shown in the figures were determined in a laboratory test during which the blood flow was adjusted to 300 ml/min, the substituate flow to 80 ml/min and the ultrafiltration rate to 100 ml/h. In the frequency spectrum, the coefficients of the first harmonic component and the harmonic components of a higher order can be recognized which are attributable to the blood pump 10 and the substituate pump 22.

The evaluation unit 50 calculates the quotient between a harmonic of a higher order, e.g. the second or third harmonic and the coefficient of the harmonic of the first order, i.e. the standardized coefficients of spectral splitting. The standardized coefficient of the substituate pump represents a first evaluation factor whereas the standardized coefficient of the blood pump represents a second evaluation factor. For comparing the evaluation factors of the substituate pump and the blood pump, the evaluation unit 50 is equipped with a further unit 50b. If the evaluation factor of the substituate pump lies substantially above the evaluation factor of the blood pump, the conclusion is drawn that postdilution is present (FIG. 5A). If the evaluation factor of the substituate pump is merely above or in the vicinity of the substituate pump or if both evaluation factors are the same, the conclusion is drawn that predilution is present (FIG. 5B). The detection of predilution or postdilution on the basis of the comparison of the evaluation factors takes place in a facility 50c.

The facility 50c for recognizing predilution or postdilution is equipped with a facility for forming the difference between the two evaluation factors. The difference is compared with a predetermined limit value which is determined such that a reliable distinction can be made between predilution and postdilution. A postdilution is present if the difference between the first and the second evaluation factor is greater than the predetermined limit value and a predilution is present if the difference between the first and the second evaluation factor is less than the predetermined limit value. The result can be indicated in an optical and/or acoustic display unit which is not illustrated.

What is claimed is:

1. A device for the extracorporeal treatment of blood comprising:
a dialyser or filter divided by a membrane into a first chamber and a second chamber;
an extracorporeal blood stream including the first chamber;
a fluid system including the second chamber;
a substituate pump connected to a substitution fluid line leading to the extracorporeal blood stream upstream or downstream of the dialyser or the filter; and
a device configured to determine if a substitution fluid is supplied upstream or downstream of the dialyser or filter, wherein the device comprises:
a control unit for at least one of shutting off the substituate pump and starting up the substituate pump;
a measuring unit for measuring the pressure in the extracorporeal blood stream downstream of the dialyser or the filter; and
a means for detecting a supply of substitution fluid upstream or downstream of the dialyser or the filter by determining an increase or decrease in the pressure after at least one of the shutting off the substituate pump which has been previously started up and the starting up the substituate pump which has been previously shut off.

2. The device according to claim 1 wherein:
for the detection of the supply of substitution fluid, the control unit is configured to shut off the substituate pump which has been previously started up, and after a predetermined time interval has passed, to start up the substituate pump; and
the means for detecting is configured such that a supply of substitution fluid upstream or downstream of the dialyser or the filter is detected on the basis of a change between a previous pressure increase and a subsequent pressure drop, or is detected on the basis of a change between a previous pressure drop and a subsequent pressure increase.

3. The device according to claim 2 wherein:
the means for detecting is configured to determine that the supply of substitution fluid is downstream of the dialyser or the filter if a first pressure increase followed by a second pressure drop is detected.

4. The device according to claim 2 wherein:
the means for detecting is further configured to determine that the supply of substitution fluid is upstream of the dialyser or the filter if a first pressure drop followed by a second pressure increase is detected.

5. The device according to claim 2 wherein:
the measuring unit comprises a pressure sensor.

6. The device according to claim 5 wherein:
the means for detecting comprises a low-pass filter configured to receive a pressure signal of the pressure sensor, and a comparator configured to compare a filtered output signal of the pressure sensor with at least one of a predetermined upper limit value and a predetermined lower limit value.

7. A device for the extracorporeal treatment of blood comprising:
a dialyser or filter divided by a membrane into a first chamber and a second chamber;
an extracorporeal blood stream including the first chamber;
a fluid system including the second chamber;
a substituate pump that produces an oscillating pressure signal, said substituate pump arranged in a substitution fluid line, said substitution fluid line leading to the extracorporeal blood stream upstream or downstream of the dialyser or the filter; and
a device configured to determine if a substitution fluid is supplied upstream or downstream of the dialyser or filter, wherein the device comprises: a measuring unit for measuring the pressure in the extracorporeal blood stream downstream of the dialyser or the filter; and
an evaluation unit comprising:
a means for performing a frequency analysis of the oscillating pressure signal;
a means for obtaining a value attributable to the substituate pump based on the frequency analysis;
a means for comparing the value attributable to the substituate pump to a characteristic reference signal; and
a means for determining if the substitution fluid is supplied upstream or downstream of the dialyser or the filter by a comparison of the value attributable to the substituate pump to the characteristic reference signal.

8. The device according to claim 7 further comprising:
a blood pump that produces an oscillating pressure signal for conveying the blood, wherein the blood pump is arranged in the extracorporeal blood stream upstream of the dialyser or the filter;
wherein the evaluation unit further comprises:
a means for obtaining a value attributable to the blood pump based on the frequency analysis;
wherein the value attributable to the blood pump is the characteristic reference signal and the means for determining can determine on the basis of a comparison of the value attributable to the substituate pump to the value attributable to the blood pump.

9. The device according to claim 7 wherein:
said frequency analysis is a Fourier analysis.

10. The device according to claim 7 wherein:
the means for performing a frequency analysis is configured such that:
at least one first evaluation factor is determined from at least one quotient of at least one harmonic component of a higher order and at least one harmonic component of a lower order of the substituate pump; and
the means for comparing the value attributable to the substituate pump to a characteristic reference signal is configured such that the at least one first evaluation factor and the characteristic reference signal can be compared.

11. The device according to claim 7 wherein:
the means for determining if the substitution fluid is supplied upstream or downstream of the dialyser or the filter is configured to determine that the supply of a substitution fluid is downstream of the dialyser or the filter if the difference between the at least one first evaluation factor and the at least one second evaluation factor is greater than a predetermined value.

12. The device according to claim 7 wherein:
the means for determining if the substitution fluid is supplied upstream or downstream of the dialyser or the filter is configured to determine that the supply of a substitution fluid is upstream of the dialyser or the filter if the difference between the at least one first evaluation factor and the at least one second evaluation factor is smaller than a predetermined value.

13. The device according to claim 7 wherein:
the means for performing a frequency analysis is configured such that:
at least one first evaluation factor is determined from at least one quotient of at least one harmonic component of a higher order and at least one harmonic component of a lower order of the substituate pump; and
at least one second evaluation factor is determined from at least one quotient of at least one harmonic component of a higher order and at least one harmonic component of a lower order of the blood pump; and
the means for comparing the value attributable to the substituate pump to a characteristic reference signal is configured such that the at least one first evaluation factor and the at least one second evaluation factor can be compared.

* * * * *